United States Patent
Shrivastav et al.

(10) Patent No.: US 12,024,748 B2
(45) Date of Patent: Jul. 2, 2024

(54) N-MYRISTOYLTRANSFERASE (NMT)1, NMT2 AND METHIONINE AMINOPEPTIDASE 2 OVEREXPRESSION IN PERIPHERAL BLOOD AND PERIPHERAL BLOOD MONONUCLEAR CELLS IS A MARKER FOR ADENOMATOUS POLYPS AND EARLY DETECTION OF COLORECTAL CANCER

(71) Applicant: VASTCON, Winnipeg (CA)

(72) Inventors: Shailly Varma Shrivastav, Winnipeg (CA); Anuraag Shrivastav, Winnipeg (CA)

(73) Assignee: Vatscon, Winnipeg (CA)

( * ) Notice: Subject to any disclaimer, the term of this patent is extended or adjusted under 35 U.S.C. 154(b) by 142 days.

(21) Appl. No.: 16/098,948

(22) PCT Filed: May 3, 2017

(86) PCT No.: PCT/CA2017/050538
§ 371 (c)(1),
(2) Date: Nov. 5, 2018

(87) PCT Pub. No.: WO2017/190241
PCT Pub. Date: Nov. 9, 2017

(65) Prior Publication Data
US 2019/0093168 A1    Mar. 28, 2019

Related U.S. Application Data

(60) Provisional application No. 62/331,045, filed on May 3, 2016.

(51) Int. Cl.
*C12Q 1/6883* (2018.01)
*G01N 33/573* (2006.01)
*G01N 33/574* (2006.01)

(52) U.S. Cl.
CPC ......... *C12Q 1/6883* (2013.01); *G01N 33/573* (2013.01); *G01N 33/57419* (2013.01); *C12Q 2600/158* (2013.01); *G01N 2333/91057* (2013.01); *G01N 2333/948* (2013.01); *G01N 2800/52* (2013.01)

(58) Field of Classification Search
CPC .................................................. C12Q 1/6883
USPC ......................................................... 435/7.1
See application file for complete search history.

(56) References Cited

U.S. PATENT DOCUMENTS 7,892,758 B2 *   2/2011   Sharma ............ G01N 33/57419
                                                    435/7.1
11,506,663 B2 *  11/2022  Shrivastav ....... G01N 33/57419

FOREIGN PATENT DOCUMENTS

WO      2014062845        4/2014
WO      WO 2014/082178 A1 *  6/2014
WO      2015172249        11/2015

OTHER PUBLICATIONS

Selvakumar, P. et al. "Role of calpain and caspase system in the regulation of N-myristoyltransferase in human colon cancer (Review)" International Journal of Molecular Medicine, May 2007, vol. 19 Issue 5, pp. 823-827 (Year: 2007).*
Shrivastav et al (Journal of Translational Medicine, 2005, 5(58): 1-6).*
Raju et al (Exp Cell Res, 1997, 235: 145-154).*
Ko et al (The American Journal of Medicine, 2010, 123(6): 528-535).*
Aoki et al (Clinical & Developmental Immunology, 2006, 13(2-4): 265-271).*
Ransohoff et al (NEJM, 1991, 325(1): 37-41).*
Selvakumar P. et al: High Expression of Methionine Amniopetidase 2 in Human Colorectal Adenocarcinomas, Clinical Cancer Research, American Association for Cancer Research, US, vol. 10, No. 8, Apr. 15, 2014, pp. 2771-2775, XP002351173, ISSN:P 1078-0432. CCR-03-0218.
Selvakumar et al: Potential Role of N-Myristoyltransferase in Cancer, Progress in Lipid Resea, Pergamon Press, Paris, France, vol. 46, No. 1. Nov. 22, 2006, pp. 1-36, XP005776871, ISSN: 0163-7827, DOI: 10.1016/J/PI;ipres. 2006.05.002.

* cited by examiner

*Primary Examiner* — Sean E Aeder
(74) *Attorney, Agent, or Firm* — Michael R Williams; Ryan W Dupuis; Ade & Company Inc.

(57) ABSTRACT

Described herein is the identification of the NMT1, NMT2 and metAP2 genes, mRNA overexpressed in PBMCs of patients with adenomatous polyps in comparison with patients with non-adenomatous polyps and healthy controls. We also discovered that NMT2 levels are higher in the PBMCs of patients adenomatous polyps in comparison with patients with non-adenomatous polyps and healthy control subjects.

5 Claims, 2 Drawing Sheets

N-MYRISTOYLTRANSFERASE (NMT)1, NMT2 AND METHIONINE AMINOPEPTIDASE 2 OVEREXPRESSION IN PERIPHERAL BLOOD AND PERIPHERAL BLOOD MONONUCLEAR CELLS IS A MARKER FOR ADENOMATOUS POLYPS AND EARLY DETECTION OF COLORECTAL CANCER

PRIOR APPLICATION INFORMATION

The instant application is a 371 of PCT Application CA2017/050538, now abandoned, which claimed the benefit of U.S. Provisional Patent Application, filed May 3, 2016, Ser. No. 62/331,045, entitled 'N-myristoyltransferase (NMT)1, NMT2 and methionine aminopeptidase 2 overexpression in peripheral blood mononuclear cells is a marker for adenomatous polyps and early detection of colorectal cancer', now abandoned, the contents of which are incorporated herein by reference.

BACKGROUND OF THE INVENTION

Cancer is the leading cause of deaths worldwide. The cancers of colon, rectum and appendix are collectively called colorectal cancer (CRC). CRC is the second or third most fatal cancer worldwide but has a 90% survival if treated at an early stage (CancerCare Manitoba, 2007; Population screening for-colorectal cancer, 2006). Yet, every year over 600,000 people around the world die of CRC (Canadian Cancer Society, 2010).

CRC arises from pre-malignant adenomatous polyps, which may take several years to develop into cancer. Both diet and genetics are involved in the aetiology of CRC. Genetic predisposition to CRC includes well-defined genetic syndromes like familial adenomatous polyposis as well as ill-defined familial aggregations; 30% of CRC cases are familial (CancerCare Manitoba, 2007; Population screening for colorectal cancer, 2006). CRC occurs in several forms, including for example adenocarcinomas, leiomyosarcoma, lymphoma, melanoma and neuroendocrine tumours. 95% of CRC are adenocarcinomas. Malignancy is the invasion of tumour through the muscularis mucosae to the sub-mucosa. The term 'adeno' means gland, carcinoma is malignant tumour of the epithelium (a sheet of cells). However, not all polyps develop into CRC and the vast majority of CRC cases are not familial. These statistics highlight an urgent unmet need of reliable screening methods for early detection of CRC right at the stage of adenomatous polyps before they can develop into advanced malignant tumours of the colon and rectum.

Current CRC Screening Strategies

Screening is the identification of individuals amongst a given population who are predisposed to develop a disease prior to the onset of symptoms. The most common screening tests for CRC include stool-based tests, sigmoidoscopy and colonoscopy (Screening, 2001) (Winawer, et al., 2003). There are a couple of options available in the market for stool-based test, including Fecal Occult Blood Testing (FOBT), Fecal Immuno Test (FIT) and stool-DNA based test.

FOBT tests for the presence of blood in the feces, which could be due to several reasons, not limited to colorectal cancer. Consequently, this test is non-specific. Prior to testing, dietary restrictions have to be followed which include avoiding vegetables that are members of Brassicaceae (cabbage family) and meats as they interfere with the test. Thus, while FOBT is cost-effective, the rates of false positives are very high.

FIT is a little more specific as it tests for the presence of human blood in stool; however, it is temperature-sensitive.

Stool DNA test screens for the presence of DNA specific to cancer cells.

All the tests described above are stool-based tests and therefore the compliance rates are low due to the nature of test.

Sigmoidoscopy and colonoscopy are invasive and expensive procedures and the results and risks of the procedure depend on the expertise of the attending endoscopist (Baxter and Rabeneck, 2009; Singh et al. 2010; Singh et al. 2009). They are not population based screening tests recommended in Canada.

In Canada, FOBT is the population-based screening tool for early detection and screening of colorectal cancer, not sigmoidoscopy and colonoscopy. The compliance rate of these tests for screening is limited due to low sensitivity or invasive nature of the test (Moayyedi, 2007; Nicholson, et al., 2005).

In Manitoba, for example, colon cancer screening has been largely unsuccessful as 85% of targeted patients choose not to undergo the process.

Importantly, these stool-based tests cannot identify the asymptomatic population that have adenomatous polyps, which could eventually develop into CRC over time. Accordingly, there is a need for such a technology, which can identify those individuals that have adenomatous polyps prior to succession into cancer. Removal of adenomatous polyps before they develop into CRC can save lives and also improve the quality of lives.

The widely available biomarker Carcinoembryonic Antigen (CEA) has limited sensitivity and specificity (Duffy, et al., 2003; Ouyang, et al., 2005). However, blood tests are likely to be more readily acceptable than stool or endoscopic tests. Cost effective blood tests may identify patients at high risk for CRC and improve patient compliance for more intensive and invasive diagnostic procedures.

N-myristoylation

N-myristoylation is the covalent attachment of a 14-carbon saturated fatty acid chain to the N-terminal glycine residue of a protein that is catalyzed by the enzyme N-myristoylatransferase (NMT). Myristoylation of proteins has been observed across diverse taxa, including that of mammals, plants, viruses and fungi (Farazai, et al., 2001). In lower eukaryotes, a single gene codes for NMT. Higher eukaryotes such as humans have two genes (Giang and Cravatt, 1998).

N-myristoylation is an irreversible co-translational protein modification (Towler, et al., 1987). Some recent reports have suggested exceptions to this rule with evidence of post-translational myristoylation. For instance, the pro-apoptotic protein BID is cleaved by Caspase 8 prior to apoptosis to reveal a myristoylation motif. Another protein that is post-translationally myristoylated is P21-activated protein kinase, which is involved in maintaining the cytoskeleton (Zha, et al., 2000; Vilar, et al., 2006). Proteins involved in signal cascades, cellular transformation and oncogenesis are often myristoylated. These include the catalytic subunit of cAMP-dependent protein kinase (Carr, et al., 1982), the β-subunit of Calcineurin (Aitken, et al., 1982), the α-subunit of several G-proteins (Schultz, et al, 1987), the cellular transforming forms of $pp^{60-src}$ (Schultz, et al., 1985), several tyrosine kinases and proteins important for assembly, maturation and infectivity of mature virus particles, such as murine leukemia virus Pr65gag precursor (Rein, et al., 1986) and poliovirus VPO polypeptide precursor (Marc, et al., 1989).

NMT Overexpression in CRC

Eukaryotic NMT is a member of the GCN5-related N-acetyltransferase (GNAT) superfamily of proteins (Resp, 1999) (Boutin, 1997) (Farazai, et al., 2001). N-acetyltransferase uses acetyl coenzyme A (CoA) to transfer an acetyl group from the donor to the primary amine of the acceptor. Two genes encode NMT in higher eukaryotes such as bovine, human and plants. The second genetically distinct NMT 2 cDNA (NMT-2) has been cloned from a human liver library. The respective mouse homologues for the two human NMTs have also been cloned (Giang DK et al., 1998, J Biol Chem.;273:6595-8).

Elevated activity of NMT has been reported in colonic tumour tissue as compared to tissue adjacent to the tumour and tissue from control patients (Magnuson, et al., 1995). Recent studies have also shown that NMT1 expression in colonic tumours is higher during the early stages of colon cancer, and is also high in polyps (Selvakumar, et al., 2006). However, in previous studies, measurements of NMT activity and expression in tumour tissues by IHC were most likely depicting total NMT expression instead of just NMT1 (King & Sharma, 1991). We have demonstrated that NMT2 levels were elevated in the PBMCs of CRC patients in comparison with healthy control individuals.

NMT Overexpression

NMT overexpression in colonic tumours is not well understood. However, it is consistent with the increased demands for myristoylation of oncoproteins in response to rapid cell division during tumorigenesis. A link between CRC and the immune system can be established through their respective demands of NMT. NMT activity and NMT1 expression has been found to be essential for the proper development of monocytic lineage, and therefore may be involved in the differentiation of other leukocytes (Shrivastav, et al., 2008). Shrivastav et al. (2007) established strong positive NMT1 immunostaining in CRC peripheral blood of CRC patients (n=18). The immune-staining was performed using polyclonal antibodies that were raised against full length NMT1 protein.

The expression pattern of NMT1 and NMT2 isoforms (products of two different genes) in PBMC of CRC patients using antibodies specific to NMT1 or NMT2 showed that NMT2 protein and not NMT1 protein is overexpressed in the PBMC of CRC patients. NMT2 protein is the product of a different gene than NMT1. Upon further isolation of T-cells from PBMC we clearly established that NMT2, not NMT1, is overexpressed in T cells of CRC patients.

Methionine Aminopeptidase (MetAP) Expression:

Aminopeptidases are metalloproteases and are responsible for the removal of amino acids from the unblocked N-terminus of proteins. Protein synthesis is initiated by a start codon that codes for the amino acid methionine in eukaryotes and formylmethionine in the case of prokaryotes. Methionine aminopeptidase (MetAP) is an enzyme that catalyzes the removal of methionine of the newly synthesized protein. Methionine removal is an essential step prior to further N-terminal modifications such as acetylation and myristoylation. Human MetAP exists in two isoforms: MetAP1 and MetAP2, which are coded by different genes. Isoforms of MetAP2 differ in substrate specificity, expression control and are not redundant in function. In various cells, MetAP1 is constitutively expressed whereas MetAP2 is involved in the regulation of cell proliferation. MetAP1 plays an important role in cell division. Studies have demonstrated that inhibition of MetAP1 results in the apotosis in HeLa and HT1080 cells.

Studies have demonstrated that MetAP2 plays an important role in growth of several types of tumours. Treatment with antisense MetAP2 induces apoptosis in rat hepatoma cells. Higher MetAP2 levels have been found in malignant mesothelioma, malignant lymphomas and esophageal squamous carcinomas. Fumagillol, an inhibitor of angiogenesis has been reported to supress MetAP2 expression in human neuroblastoma. Earlier, we demonstrated that MetAP2 levels were higher in the PBMCs of colorectal cancer patients. This was demonstrated using immunohistochemistry as well as PCR.

SUMMARY OF THE INVENTION

According to an aspect of the invention, there is provided a method of identifying a candidate for polyp removal comprising:
measuring N-myristoylatransferase 1 (NMT1), NMT2 and/or MetAP2 expression levels in a peripheral blood or peripheral blood mononuclear cell sample from a patient, wherein NMT1, NMT2 and/or MetAP2 expression levels above a threshold level indicates that the patient is a candidate for polyp removal.

According to another aspect of the invention, there is provided a method of determining if a patient is a candidate for polyp removal comprising:
measuring N-myristoylatransferase 2 levels in a peripheral blood or peripheral blood mononuclear cell sample from a patient, wherein NMT2 levels above a threshold level indicates that the patient harbours adenomatous polyps and is a candidate for adenomatous polyp removal.

DESCRIPTION OF THE PREFERRED EMBODIMENTS

Figure 1:
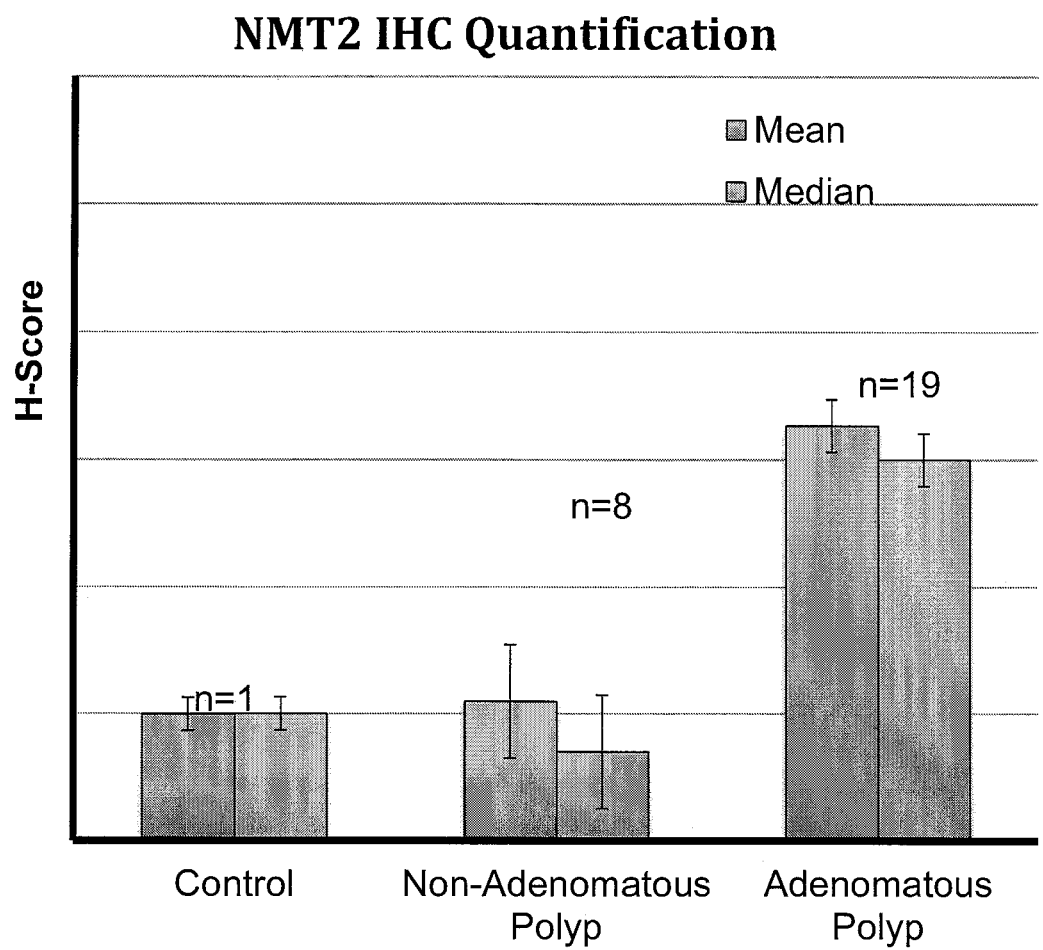
FIG. 1: NMT2 expression in peripheral blood mononuclear cells. PBMCs were isolated, cytospins were made on glass slide and immunohistochemical analysis was performed and H-score was done as described herein. The graph represents the average H-score of NMT2 staining in healthy controls (n=19), non-adenomatous polyps (n=8) and adenomatous polyps (n=19). NMT2 levels in adenomatous polyps are ~3.5-fold higher than control subjects or subjects with non-adenomatous polyps.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Previously, it was reported that NMT1, NMT2 and MetAP2 proteins were overexpressed in PBMC of colorectal cancer patients in comparison with healthy controls due to positive immunostaining. Although detection of NMT1 was performed by using polyclonal antibody raised against full length NMT1 protein that shares 77% amino acid sequence homology with NMT2. We also observed that the mRNA of NMT2 and MetAP2 were higher in CRC patients in comparison with healthy controls.

Colorectal cancer develops over a period of several years from adenomatous polyps. Identification and removal of adenomatous polyps before they can develop into cancer is of high relevance. In the current study, the inventors demonstrate that NMT1, NMT2 and MetAP2 expression levels are higher in PBMCs of patients with adenomatous polyps in comparison with healthy individuals or individuals with non-adenomatous polyps. NMT1, NMT2 and MetAP2 may be measured for example by using a primer or probe comprising of a nucleic acid sequence unique to NMT1, NMT2 and/or MetAP2.

The inventors also demonstrate that NMT2 protein levels are higher in peripheral blood or PBMCs of patients with adenomatous polyps compared to healthy control individuals or patients with non-adenomatous polyps. This was demonstrated using an antibody specific for NMT2.

As will be appreciated by one of skill in the art, given the high impact of CRC, there is an urgent need for a more convenient, more accurate and cost-effective screening test that could triage patients for more intensive procedures such as colonoscopy. This would improve patient compliance and clinical outcomes with resulting significant impact on both population health and health care costs. A blood based screening test is an attractive alternative as has been demonstrated with screening tests for prostate cancer and lipids for heart disease.

Furthermore, a screening test which detects pre-malignant polyps provides the extraordinary opportunity not only to identify early, but also to actually prevent cancer since patients with since positive screening tests for pre-malignant lesions can be followed up with colonoscopy to remove these lesions before developing cancer.

The inventors used validated polyclonal prestige antibodies from Sigma (Canada), which are specific to NMT2.

As will be appreciated by one of skill in the art, patient samples for such a screening process can be obtained from a portion of samples gathered for routine blood work. Because of the relatively low cost of the screen, any individual who has a blood sample drawn can be screened for the presence of polyps. This in turn means that more pre-cancerous polyps can be removed, thereby reducing the occurrence of CRC.

The further adenomatous polyp screening method may be selected from the group consisting of individuals undergoing sigmoidoscopy and colonoscopy. That is, individuals who are candidates for sigmoidoscopy or colonoscopy may be screened using one of the methods of the invention first, to determine if further screening is necessary, as discussed herein; alternatively, individuals who are diagnosed with polyps through any means may be subjected to one of the methods of the invention to determine if the polyps are adenomatous, as discussed herein. Alternatively, as discussed herein, an individual in whom polyps are detected may be immediately scheduled for a colonoscopy to remove the polyps.

The patient may be a human.

The patient may have a familial history of colorectal cancer, high risk or predisposed to CRC or be older than 55.

The sample may be whole blood, peripheral blood or peripheral blood mononuclear cells.

As discussed herein, the biological basis for NMT1, NMT2 and MetAP2 gene overexpression in the PBMC of patients predisposed to CRC or CRC patients has to be better characterized to be utilized as a marker for the asymptomatic population having adenomatous polyps, which could later develop into CRC.

As discussed below, described herein is the discovery that the NMT1, NMT2 and MetAP2 genes, mRNA or protein are overexpressed in PBMCs of patients with adenomatous polyps.

As discussed herein, it was previously discovered that NMT2 is elevated in PBMC of individuals who have CRC. However, the discovery that NMT1, NMT2 and MetAP2 are overexpressed in PBMC during earlier oncogenic or pre-oncogenic changes in the colon and rectum is surprising and allows for the identification of individuals who are at risk of developing CRC and should be monitored more closely rather than detecting individuals who have developed CRC. As discussed above, CRC is the second or third most fatal cancer worldwide but has a 90% survival if treated at an early stage.

As used herein, "expression", "over-expression", "levels" or "expression levels" refer to either transcription levels or protein levels or both.

As discussed herein, the measuring reagent may be a primer, probe or antibody specific for NMT1, NMT2 and/or MetAP2.

According to an aspect of the invention, there is provided a method of identifying a candidate for further colorectal cancer (CRC) screening comprising:

measuring N-myristoylatransferase 1 (NMT1), NMT2 and/or MetAP2 expression levels in a sample from a patient, wherein NMT1, NMT2 and/or MetAP2 expression levels above a threshold level indicates that the patient is a candidate for further CRC screening.

According to another aspect of the invention, there is provided a method of identifying a candidate for polyp removal comprising:

measuring N-myristoylatransferase 1 (NMT1), NMT2 and/or MetAP2 expression levels in a peripheral blood or peripheral blood mononuclear cell sample from a patient, wherein NMT1, NMT2 and/or MetAP2 expression levels above a threshold level indicates that the patient has polyps.

In some embodiments, the patient is scheduled for a procedure to remove the polyps.

In some embodiments, the polyps are removed by a colonoscopy or similar procedure.

The patient may be a patient who is in need of or desirous of screening for adenomatous polyps. As will be appreciated by one of skill in the art, a patient who is in need of or desirous of screening for adenomatous polyps may be an individual above a certain age, for example, older than 55 years of age, or may be an individual who is at risk of developing CRC or polyps. An individual who is at risk of developing CRC or polyps as used herein may refer to an individual who has a familial history or a personal history of CRC or adenomatous polyp development, or other indications that may lead to adenomatous polyps or CRC, or an individual who is considered to be at risk of CRC or adenomatous polyp development by virtue of one or more additional risk factors, such as obesity, smoking, a low fiber diet or other risk factors known in the art or combinations thereof.

In some embodiments, the patient is an individual who is at risk of developing polyps for example adenomatous polyps. For example, an individual or a patient who is considered to be at risk of adenomatous polyp development may be an individual who has one or more additional risk factors, such as but by no means limited to age, familial history of CRC, familial history of adenomatous polyp development, obesity, smoking, a low fiber diet or other risk factors known in the art or combinations thereof.

According to another aspect of the invention, there is provided a method of measuring N-myristoylatransferase 2 (NMT2) expression in a sample from a patient comprising:

measuring N-myristoylatransferase 2 levels in a sample from a patient by using a measuring reagent which is directed to unique or specific regions of NMT2 and determining if NMT2 levels are above a threshold level.

According to an aspect of the invention, there is provided a method of determining if a patient is a candidate for polyp removal comprising:

measuring N-myristoylatransferase 2 levels in a sample from a patient, wherein NMT2 levels above a threshold level indicates that the patient harbours adenomatous polyp and is a candidate for adenomatous polyp removal.

In some embodiments, the patient is scheduled for a procedure to remove the polyps.

In some embodiments, the polyps are removed by a colonoscopy or similar procedure.

As will be appreciated by one of skill in the art, alternatively, the patient may be scheduled for further adenomatous polyp screening and/or adenomatous polyp removal. This may be carried out by any suitable screening method known in the art, for example but by no means limited to sigmoidoscopy and colonoscopy.

Preferably the patient or individual is a human.

The sample may be any suitable sample from which NMT1, NMT2 and/or MetAP2 activity can be measured. As will be appreciated by one of skill in the art, the "threshold" level referred to above will of course depend on the method of measuring NMT1, NMT2 and/or MetAP2 will also depend on the sample used in this measurement. Such a threshold may be determined by comparison with a known negative control and/or a known positive control. As will be apparent to one of skill in the art, such controls do not necessarily need to be repeated each time the assay is carried out.

Earlier it was reported that NMT1, NMT2 and MetAP2 are overexpressed in PBMC of CRC patients (Shrivastav, et al., 2007). Myristoylated proteins are involved in a range of functions, from cell division to apoptosis, but most are not well understood. Shrivastav et al. (2007) found NMT to localize in the nucleus of Bone Marrow Cells (BMC) from CRC patients and rats with colonic tumours. In control groups, NMT was cytoplasmic. Exploring the roles of NMT isoforms in CRC, Ducker et. al. (2005) examined the effects of silencing NMT1 and NMT2 using siRNA in CRC cells. Silencing NMT2 induced cell death in tumor cells 2.5 fold more as compared to silencing NMT1 (2005) which implies that NMT2 is a better therapeutic target. It has also been observed that cancer causes hematopoietic stem cells to undergo apoptotic events (Deckers, et al., 1973).

Previously we have shown that NMT2 and MetAP2 is overexpressed in the PBMCs of CRC patients compared to control subjects. However, a systematic evaluation of NMT1, NMT2 and MetAP2 expression in PBMC of individuals with different types of GI polyps were not performed. There are different types of polyps that are found in the GI tract.

The origin of "polyp" is a Greek word 'polypous' which means a 'morbid lump'. Polyps are clumps of cells that form in the inner lining of colon and protrude into the lumen of any hollow vessel for example the lumen of the intestine or colon. They usually arise from the mucosal layer of an organ system for example the gastro-intestinal tract; however, some polyps have a sub-mucosal pathology that may cause mucosal protrusion into the lumen. Polyps are epithelial and histologically polyps of colon can be classified as adenomatous polyps (also known as neoplastic polyps), hyperplastic, hamartomatous or inflammatory polyps.

1) Adenomatous Polyps:

Adenomatous polyps are also known as neoplastic polyps and are malignant. These polyps are mucous secreting therefore are glandular epithelial cells hence called adenomatous. Risk factors include smoking, obesity, high intake of red meat, low fibre and calcium. Studies have demonstrated that non-steroidal anti-inflammatory drugs (NSAIDS) and statins have inhibitory effects on polyps. Depending on the growth pattern, adenomatous polyps are sub-classified into tubular adenomas, villus adenomas, tubule-villus adenomas or serrated adenomas.

Dysplasia is a term that refers to abnormal glandular nature with damaged intracellular structure. To some extent, all adenomas exhibit dysplasia. The degree of dysplasia differs between the different types of adenomas and as it becomes severe, the carcinogenicity increases and usually correlates with villous histology and size of the polyp. High-grade dysplasia is the same as carcinoma in situ.

i) Tubular adenoma is branched tubular gland in appearance and is one of the most commonly occurring polyps. Tubular polyps are pedunculated i.e., have a stalk to which the mass is attached and demonstrate less 'atypia' (non-standard cell types) than the villus adenomas, although there is a variable degree of atypia.

ii) Villus adenomatous polyps have finger like projections (villus) and in comparison with tubular adenomatous polyps they are not as common, but can have severe atypia.

iii) Tubulo-adenomatous polyps have features of both tubular and villus polyps.

iv) Histologically, serrated adenomas have saw-tooth (papillary infolding into crypts) like appearance. They are sessile, i.e., no stalk attached to the mass. Serrated adenomas are more common in the right colon and are malignant. Serrated adenomas can be sessile serrated adenomas (SSA) or traditional serrated adenomas (TSA). Both forms of serrated polyps are malignant. Sessile serrated adenomas possess 'inverted T-shaped crypt' or dilated 'L-shaped' base. On the contrary, traditional serrated adenomas are pedunculated.

In general, the larger the polyp, the greater the chance it will be a carcinoma and invasive. Not all adenomatous polyps develop into CRC but nearly all of the malignant polyps are adenomatous. Adenomatous polyposis includes familial adenomatous polyposis, Gardner syndrome and Turcot syndrome.

2) Hyperplastic Polyps

These are the most common type of polyps and are smaller than 5 mm in diameter. Called dimunitive polyps, they are sessile. They usually don't exhibit dysplasia but show hyperplasia, and therefore are not malignant.

3) Hamartomatous polyps

Hamartomatous polyps can appear sporadically as a part of polyposis syndrome at an early age and are not malignant but are highly vascularized so can cause bleeding. These polyps can appear in children as young as 10 years old and therefore are also known as juvenile polyps. Polyposis syndrome includes juvenile polyposis syndrome, Peutz- Jeghers syndrome, Cowden syndrome, and Ruvelcaba-Myher-Smith syndrome. In this case, the polyp covers the connective tissue including smooth muscle, lamina proporia and inflammatory infiltrates are covered by hypertrophic epithelium.

4) Inflammatory Polyps

These usually occur in patients with inflammatory bowel disease, usually ulcerative colitis. The lesions are pseudopolyps (not true polyps) and are not malignant.

All CRC develop from adenomatous polyps but not all adenomatous polyps would transform into CRC. Therefore, we performed a systematic study to determine changes in the expression profile of NMT1, NMT2 and MetAP2 in PBMC of individuals with no polyps, hyperplastic polyps (non-adenomatous polyps) and adenomatous polyps. We observed that these three protein markers are overexpressed in adenomatous polyps, which suggest that immune response cells (PBMC) are sensing oncogenic changes at molecular levels in colon and rectum. These observations further indicates that although both NMT1 and NMT2 are overexpressed in PBMC during earlier oncogenic changes in colon and rectum, it is only NMT2 which remains elevated in PBMC of CRC patients. This also indicates that NMT2 elevation occurs much earlier in CRC development than previously thought.

Patient Samples

Patient samples were obtained from Health Sciences Centre, Winnipeg, Manitoba after requisite ethics approval from University of Winnipeg, University of Manitoba, Health Sciences Centre and patient consent. In total 4 controls and 4 CRC patients, and 3 patients with unusual NMT2 expression were examined. All patients have undergone colonoscopy. Polyclonal human anti-NMT2 antibodies were procured from Sigma Canada. These antibodies were prestige series validated for IHC. They are specific for NMT2.

PBMC Separation

PBMCs were isolated from samples from CRC patients or control subjects. Blood samples were carefully transferred into a 50 mL centrifuge tube and diluted with RPMI 1640 media in a 1:1 ratio. RPMI 1640 that was supplemented with 1% sodium-pyruvate, 1% L-glutamine was used for dilution of blood samples. 15 mL centrifuge tubes were used that were filled with 4 mL Ficoll. Blood was slowly poured onto the Ficoll so as not to disturb the Ficoll surface. These were centrifuged at 800 g for 30 min at room temperature. Peripheral Blood Mononuclear Cells (PBMC) float to the top of Ficoll column while red blood cells settle below it. Blood plasma settles above the PBMC layer. Plasma was removed using pipette. The PBMC layer was gently pipetted out into a 15 mL centrifuge tube and the rest was discarded. The isolated PBMC were washed twice by mixing cells in RPMI 1640 and centrifugation at 320 g for 10 min. Cells were then pelleted down and re-suspended in 3 ml of RPMI for counting. Trypan blue exclusion method was used to count viable cells. Based on the cell count the samples were diluted accordingly for cytospin fixing.

RNA Isolation

RNA was prepared using EZNA total RNA kit from Omega bio-tek according to manufacturer's protocol.

Quantitative PCR

Two-step PCR was performed. RNA extracted from BM cells were reverse tqPCR was performed using SYBR green mix. Primers for amplification of NMT1, NMT2, MetAP2 and GAPDH were obtained from BioRad.

Cytospin

Cytospin allows cells to be fixed onto slides using centrifugation. Samples containing at least 100,000 live cells suspended in 200 µL of RPMI 1640 were mounted onto slides using cytospin apparatus (cytospin chamber and clip). When put through a centrifugation cycle, the suspension fluid disperses into the filter paper on the base of the funnel and centrifugational force fixes cells onto slides.

IHC Analysis Using the Enhanced Polymer One Step (EPOS) Method

The primary antibody (rabbit anti-human) binds to antigen of interest. Multiple secondary anti-bodies (goat anti-rabbit) are bound to a dextran polymer backbone and localises around the primary antibody. Multiple Horse Radish Peroxidase enzymes are also couples to the dextran backbone. When the chromagen 3,3'-Diaminobenzidine (DAB) is introduced it is oxidised in the vicinity of the target protein to produce a dark brown stain (Dako, 2011).

IHC Analysis

Standard IHC techniques were used to localize antigens of interest i.e. NMT1 and NMT2 using polyclonal antibodies specific for NMT1 or NMT2. IHC analysis was performed on, whole blood smears, PBMC, CD4+ T cells and CD8+ T cells using automated Ventanna system at the CancerCare Manitoba, Winnipeg. The primary antibodies used in this study are: NMT1 and NMT2 (polyclonal rabbit anti-human, 1:50 dilution). HRP conjugated secondary antibodies were used that reacted with chromagen 3,3'-Diaminobenzidine (DAB) to produce a brown stain. The intensity of the DAB stain is a measure of the amount of protein present.

Quantifying IHC Results

Slides were quantified based on their IHC-score. An IHC-score (H score) is product of staining intensity (on a scale of 0 to 3, a 3 being the highest) and percentage of cells that take up the staining. For example, a sample where 90% of the cells stain positive and the stain intensity is 3, the H score is 3*90=270. H scores range from 0 to 300. Statistical analysis was done using a two-tailed T-test. A T-test is used to establish whether two sets of data being compared are part of a larger parent data set. If two sets of data belong to the same normally distributed data, then the observed differences could be due to chance. Here, a T-test is used to assess whether a difference between the H scores from control and CRC groups are a coincidence.

We have previously shown that there is an overexpression of N-myristoyl transferase in the PBMC of colorectal cancer (CRC) patients. NMT has two isoforms and we found that NMT2 is specifically overexpressed in the PBMC of CRC patients compared to control subjects. Most CRCs arise from pre-malignant adenomatous polyps, which is a growth in the inner lining of colon or rectum. All polyps cannot develop into cancer, however some polyps can develop into cancer over the course of several years.

Patients were recruited following informed consent with approval of the Research Ethics Board at the University of Manitoba. Peripheral whole blood was collected from those patients who were undergone colonoscopy at Health Science Centre, Manitoba. The blood was collected, transported and stored at −80° C. in PAXgene Blood RNA Tube (PreAnalytiX/AQIAGEN/BD company). The isolation and purification of intracellular RNA from whole blood for RT-PCR was done using PAXgene Blood RNA Kit (Cat No:762162).

RNA isolation: RNA was isolated from the blood sample according to the manufacture's protocol. Briefly, equilibrated PAXgene blood tubes to room temperature and centrifuge the PAXgene blood RNA tube for 10 minutes at 3000-5000 g. Removed the supernatant and vortexed until the pellet was dissolved. Added Buffer 1, vortex and collected the lysate to a micro centrifuge tube. The lysate was transferred to a PAXgene shredder spin column and transferred the supernatant and mix with 350 ul of 96% ethanol. Transferred the sample into the PAXgene RNA spin column and add buffer3 and centrifuged. Added DNase into the PAXgene RNA spin column and incubated. After this step, the buffer BR3 and BR4 were added to the spin column and after centrifugation, the elution buffer was added to the column and the elute was collected and proceed with cDNA synthesis and RT-PCR. RNA samples were prepared for RT-PCR as follows. Total RNA was reverse-transcribed using iScript Reverse Transcription Supermix for qPCR (Bio-Rad) in a total volume of 20 ul according to the manufacturer's instructions. The expression of NMT1, NMT2 and METAP2 was measured by using CRX Connect™ Real-Time system Cycler and CFX Manager 3.1 software (Bio-Rad). All samples were amplified in triplicate using 1xSsoAdvanced™ Universal SYBER Green Supermix Kit (Bio-Rad). The expression of NMT1, NMT2 and METAP2 genes were quantified relative to the house-keeping genes GAPDH and β-actin, whose expression does not change under experimental conditions.

Figure 2:
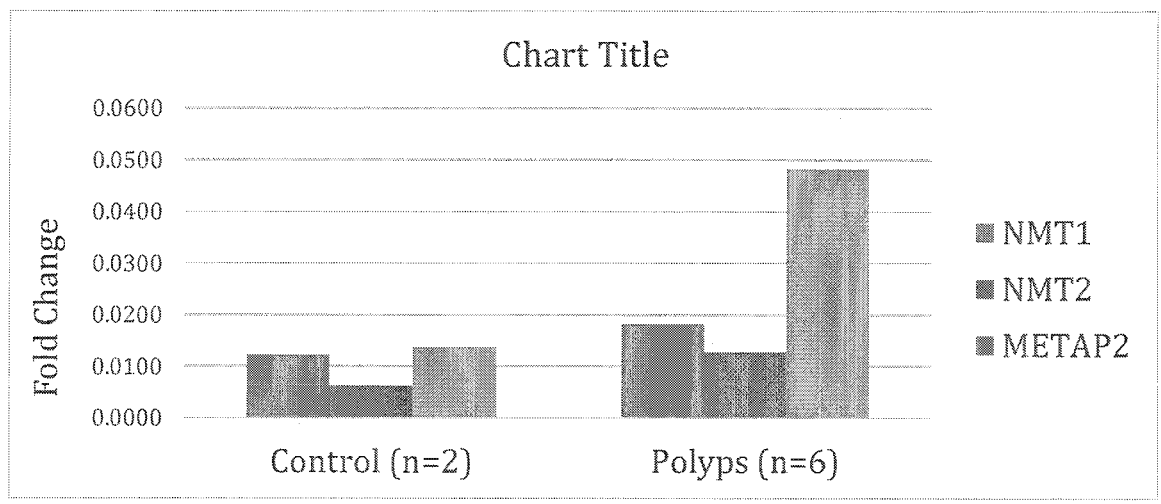
FIG. 2. Gene expression as determined by RT-PCR: The expression of NMT1, NMT2 and METAP2 genes were quantified relative to the house-keeping genes GAPDH and β-actin, whose expression does not change under experimental conditions.

As shown in FIG. 2, the results show fold change in the NMT1, NMT2 and METAP2 gene expression in patients with polyps compared to control subjects. Interestingly NMT1, NMT2 and METAP2 were overexpressed in polyps compared to control subjects. Previously our lab has shown that NMT2 is over expressed in CRC patients. However, this result shows that in polyp samples, METAP2 was significantly overexpressed compared to NMT1 or NMT2. We will further investigate this with a large number of samples to monitor the NMT1, NMT2 and METAP2 gene expression.

The scope of the claims should not be limited by the preferred embodiments set forth in the examples, but should be given the broadest interpretation consistent with the description as a whole.

REFERENCES

Aitken, A., Cohen, P. & Santikarn, S., 1982. Identification of the NH2-terminal blocking group of calcineurin B as myristic acid. FEBS Letter, pp. 314-8.
Anon., 2006. Population screening for colorectal cancer. Drug ThurBull, Volume 44, pp. 65-68.
Baxter, N. & Rabeneck, L., 2009. Is the effectiveness of colonoscopy "good enough" for population based screening?. J Natl Cancer Inst, pp. 70-1.
Boutin, J., 1997. Myristoylation. Cell Signal, pp. 15-35.
Canadian Cancer Society, 2010. Canadian Cancer Society's Steering Committee. Toronto, Cancer Statistics.
CancerCare Manitoba, 2007. Cancer in Manitoba: 2004 Annual Statistics Report, Winnipeg: s.n.
Carr, S. et al., 1982. n-Tetradecnoyl is the NH2-terminal blocking group of the catalytic subunit of cyclic AMP-dependent protein kinase from bovine cardiac muscle. USA, s.n., pp. 6128-31.
Deckers, P., Davis, R., Parker, G. & Mannick, J., 1973. The effect of tumour size on concomitant tumour immunity. CancerRes, pp. 33-9.
Duffy, M., Dalen, A. & Haglund, C., 2003. Clinical utility of biochemical markers in colorectal cancer: European Group on Tumour Marker guidelines. Eur J Cancer, pp. 718-27.
Farazai, T., Waksman, G. & Gordon, J., 2001. The biology and enzymology of protein N-myristoylation. J Biol Chem, pp. 39501-4.
Furuishi, K. et al., 1997. Blockage of N-myristoylation of HIV-1 gag induces the production of impotent progeny virus, Biochem. Biophys. Res. Commun., pp. 504-511.
Giang, D. & Cravatt, B., 1998. A second mammalian N-myristoyltransferase. J Bid Chem, pp. 6595-8.
Irving, K., 2010. Tumour immunology: Tumours support the T cell response. Nature Reviews Immunology, p. 617.
King, M. & Sharma, R., 1991. NMT assay using phosphocellulose paper binding. Anal Biochem, pp. 149-53.
Kumar, A. & Singh, S., 1995. Effect of cisplatin administration on the proliferation and differentiaion of bone marrow cells of tumour-bearing mice. Immunol Cell biol, pp. 220-5.
Magnuson, B., Raju, R., Moyana, T. & Sharma, R., 1995. Increased N-myristoyltransferase activity observed in rat and human colonic tumours. J Natl Cancer, pp. 1630-5.
Marc, D. et al., 1989. Role of myristoylation of poliovirus capsid protein VP4 as determined by site-directed mutagenesis of its N-terminal sequence. Embo K, pp. 2661-8.
Martin, D., Beauchamp, E. & Berthiaume, L., 2011. Post-translational myristoylation: Fat matters in cellular life and death. Biochimie, pp. 18-31.
Maurer-Stroh, S. & Eisenhaber, F., 2004. Myristoylation of viral and bacterial proteins. Trends Microbiol, pp. 178-185.
Moayyedi, P., 2007. Colorectal cancer screening lacks evidence of benefit. Cleve Clin J Med, pp. 549-550.
Nicholson, F., Barro, J. & Atkin, W., 2005. Population screening for colorectal cancer. Aliment Pharmacol Ther, pp. 1069-77.
Orkin, S. & Zon, L., 2008. Hematopoiesis: An Evolving Paradigm for Stem Cell Biology. Cell, pp. 631-644.
Ouyang, D., Chen, j., Getzenberg, R. & Schoen, R., 2005. Noninvasive testing for colorectal cancer: a review. Am J Gastroenterology, pp. 1393-403.
Rajala, R. et al., 2000. Increased expression of NMT in gallbladder carcinomas. Cancer, pp. 1992-9.
Rein, A. et al., 1986. Myristoylation site in Pr65gag is essential for virus particle formation by moloney nurine leukemia virus.. USA, s.n., pp. 7246-50.
Resh, M., 1999. Fatty acylation of proteins—new insights into membrane targeting of myristoylated and palmitoylated proteins. Biochim Biophys Acta, Volume 1451, pp. 1-16.
Resh, M., 2004. A myristoyl switch regulates the membrane binding of HIV-1 Gag., sI., Proc Natl Acad Sci, pp. 417-8.
Schultz, A. et al., 1987. Hydroxylanime-stable covalent linkage of myristic acid in G0 alpha, a guanine nucleotide-binding protein of bovine brain. Biochem Biophys Res Commun, pp. 1234-9.
Schultz, A. et al., 1985. Amino terminal myristoylation of the protein p60src, a retroviral transforming protein. Science, pp. 427-9.
Screening, C. C., 2001. Reccomendation statement from the Canadian Task force on Preventive Health Care. CMAJ, Issue 165, pp. 206-208.
Seaton, K. & Smith, C., 2008. N-Myristoyltransferase isozymes exhibit differential specificity for human immunodeficiency virus type 1 Gag and Nef. J. Gen. Virol., pp. 288-296.
Selvakumar, P., Smith-Windsor, E., Bonham, K. & Sharma, R., 2006. N-myristoyltransferase 2 expression in human colon cancer: cross-talk between the caplain and caspase system. FEBS Letter, pp. 2021-6.

Shrivastav, A., Varma, S. & Lawman, Z., 2008. Requirement of NMT1 in the development of monocytic lineasge. J Immunol, pp. 101.9-28.

Shrivastav, A. et al., 2007. N-myristoylatransferase: a potential novel diagnostic marker for colon cancer. J Trans Med, p. 58.

Shrivastav A, Suri SS, Mohr R, Janardhan K S, Sharma R K, Singh B. Expression and activity of N-myristoyltransferase in lung inflammation of cattle and its role in neutrophil apoptosis. Vet Res. 2010;41:9.

Singh, H. et al., 2010. The reduction in colorectal cancer mortality after colonoscopy varies by site of cancer. Gastroenterology.

Singh, H. et al., 2009. Predictors of colorectal cancer after negative colonoscopy: a population-based study. Am J Gastroenterology, pp. 663-73.

Towler, D., Adams, S. & Eubanks, S., 1987. Purification and myristoylation of yeast myristoyl CoA: protein N-myristoyltransferase. USA, s.n., pp. 2708-12.

Vilar, G. et al., 2006. Posttranslational myristoylation of caspase-activated p21-activated protein kinase 2 potentiates late apoptotic events. USA, s.n., pp. 6542-7.

Winawer, S. et al., 2003. Colorectal cancer screening and surveilance: clinical guidelines and rationale-Update based on new evidence. Gastroenterology, Volume 124, pp. 544-560.

Yang, S. et al., 2005. N-myristoyltransferase 1 is essential in early mouse development. J Biol chem, pp. 18990-5.

Zha, J. et al., 2000. Posttranslational N-myristoylation of BID as a molecular switch for targeting mitochondria and apoptosis. Science, pp. 1761-5.

The invention claimed is:

1. A method of identifying a candidate for pre-cancerous polyp removal comprising:
   measuring N-myristoylatransferase 1 (NMT1), NMT2 and MetAP2 expression levels in a peripheral blood or peripheral blood mononuclear cell sample from a patient, wherein NMT1, NMT2 and MetAP2 expression levels each above a respective threshold level indicates that the patient is a candidate for pre-cancerous polyp removal,
   wherein if the patient is a candidate for pre-cancerous polyp removal, at least one pre-cancerous polyp is removed by a colonoscopy, and
   wherein the removal of the pre-cancerous polyp prevents the pre-cancerous polyp from developing into colon cancer.

2. The method according to claim 1 wherein the NMT1, NMT2 and metAP2 genes levels are measured using at least one primer comprising nucleic acid sequences unique to NMT1, NMT2 and metAP2 respectively.

3. The method according to claim 1 wherein the NMT1, NMT2 and metAP2 gene levels are measured using a probe comprising nucleic acid sequence unique to NMT1, NMT2 and metAP2 respectively.

4. The method according to claim 1 wherein the patient is a human.

5. The method according to claim 1 wherein the pre-cancerous polyp is pre-malignant.

* * * * *